United States Patent
Rogosnitzky

(10) Patent No.: US 8,652,509 B2
(45) Date of Patent: Feb. 18, 2014

(54) METHOD OF WOUND HEMOSTASIS USING LIQUID GALLIUM NITRATE

(76) Inventor: Moshe Rogosnitzky, Telz Stone (IL)

( * ) Notice: Subject to any disclaimer, the term of this patent is extended or adjusted under 35 U.S.C. 154(b) by 196 days.

(21) Appl. No.: 12/910,831

(22) Filed: Oct. 24, 2010

(65) Prior Publication Data

US 2011/0104246 A1    May 5, 2011

Related U.S. Application Data

(60) Provisional application No. 61/257,424, filed on Nov. 2, 2009.

(51) Int. Cl.
*A61F 13/00* (2006.01)
*A61K 9/70* (2006.01)
*A61L 15/16* (2006.01)
*A61L 15/00* (2006.01)
*A61K 33/24* (2006.01)
*A01N 59/16* (2006.01)

(52) U.S. Cl.
USPC ........... 424/443; 424/444; 424/445; 424/446; 424/447; 424/650

(58) Field of Classification Search
None
See application file for complete search history.

(56) References Cited

U.S. PATENT DOCUMENTS

| | | | | | |
|---|---|---|---|---|---|
| 3,464,413 | A | * | 9/1969 | Goldfarb et al. | 604/306 |
| 4,529,593 | A | * | 7/1985 | Warrell et al. | 424/650 |
| 4,891,359 | A | * | 1/1990 | Saferstein et al. | 424/499 |
| 6,165,514 | A | * | 12/2000 | Bockman et al. | 424/495 |

OTHER PUBLICATIONS

Ginsberg et al. "Reduced surface expression and binding of fibronectin by thrombin-stimulated thrombasthenic platelets", J. Clin. Invest, vol. 71, Mar. 1983, 619-624.*
Al-Belasy et al. "Hemostatic effect of n-butyl-2-cyanoacrylate (histoacryl) glue in warfarin-treated patients undergoing oral surgery", J. Oral Maxillofac Surg 61:1405-1409, 2003.*
Sisken and Morasca, "Intrapopulation Kinetics of the Mitotic Cycle", Journal of Cell Biology, May 1, 1965, p. 179-189.
Samudrala, "Topical Hemostatic Agents in Surgery: A Surgeon's Perspective" AORN Journal Sep. 2008; 88 (3):S2-11.

* cited by examiner

*Primary Examiner* — Isis Ghali

(57) ABSTRACT

A pharmaceutical composition and method for topical wound treatment by topical treatment with gallium salts, preferably gallium nitrate. In a preferred embodiment, the gallium nitrate is in an aqueous form without coagulation inhibitors such as citrate. The aqueous gallium salt formulation may be administered by a variety of methods including spraying, topical lotions, topical foams, and/or bandages containing or packaged with breakable ampoules of aqueous gallium salt formulations, and liquid bandage formulations. The aqueous gallium salt formulation may additionally contain other active and inactive ingredients, such as viscosity modifying agents, foaming agents, antiseptics, antibiotics, enzymes, fibrinogen, fibrin, polymers and growth factors.

16 Claims, 3 Drawing Sheets

METHOD OF WOUND HEMOSTASIS USING LIQUID GALLIUM NITRATE

CROSS-REFERENCE TO RELATED APPLICATIONS

This application claims the priority benefit of U.S. provisional application 61/257,424, "METHOD OF WOUND TREATMENT USING LIQUID GALLIUM NITRATE", inventor Moshe Rogosnitzky, filed Nov. 2, 2009.

BACKGROUND OF THE INVENTION

Much research and medical effort has been devoted to the treatment of open wounds in the body. Almost immediately, starting within seconds after the skin barrier formed by the epidermis and dermis are breached; the body begins a process of healing and repair.

Here many different biochemical systems operate. Platelets start to adhere to exposed collagen fibers on the damaged tissue, releasing various factors that in turn activate other platelets, as well as portions of the blood coagulation system. Tissue factor and phospholipids, released by damaged blood vessel endothelium cells in the vicinity of the breach, form natural thromboplastin which stimulates a series of blood coagulation proteases that start to generate strands of fibrin which in turn adhere to the activated platelets, and start to form a plug, needed to control bleeding and reestablish hemostasis.

In a small wound, where there is a proportionally large amount of damaged tissue relative to the volume of the wound, this process operates quickly and efficiently. However for larger wounds, where the ratio of the damaged tissue relative to the volume of the wound, is less, this process operates at a much slower rate. Thus the time required for formation of a platelet-fibrin plug may be unacceptably long, resulting in a substantially larger (and occasionally lethal) amount of blood loss, as well as greater opportunity for pathogen entry and subsequent infection and damage.

In a slower inflammatory reaction, usually occurring after hemostasis has been established, various white blood cells, called phagocytes (dendritic cells, macrophages, monocytes, neutrophils) begin the process of engulfing and removing pathogens and debris, and in the process releasing various growth factors that start to stimulate cells near the wound to begin to proliferate.

In the proliferation stage, which usually takes place over a number of days or even weeks, fibroblasts and new blood vessels grow, a new matrix is established, and epithelial cells grow and start to reestablish the epidermis.

Finally, during the remodeling phase, collagen fibrils which were originally placed in a rather haphazard pattern during the earlier stages of the healing process, are realigned to better match up with the lines of tension in that particular area, and excess cells undergo apoptosis and are removed.

Although the wound healing process is thus a long and complex multi-stage operation, from the standpoint of immediate medical care, emergency medicine and surgery, the initial stages of establishing hemostasis are particularly critical. Thus much prior art has been devoted to these areas, particularly in the area of bandage and wound dressing technology.

In addition to the prior art devoted to various type of bandage and wound dressing technology, other prior art has focused on the use of various chemical and biochemical methods to promote hemostasis. One method is the use of various blood coagulation stimulating materials (often proteins such as fibrinogen, thrombin, and/or other coagulation factors) to produce hemostatic bandages or foams.

Gallium Nitrate

Gallium, which is immediately below aluminum in the periodic table of elements, has previously attracted medical interest, and is indicated for therapeutic use for various disorders including bone resorption disorders, autoimmune disease, cancer, and infectious disease. These previous uses are summarized by Bernstein, "*Mechanisms of Therapeutic Activity for Gallium*", Pharmacological Reviews 50(4), 1998, pages 665-682.

In aqueous solution, gallium is usually in ionic form, such as $Ga^{3+}$. Similarities between the ionic forms of gallium $Ga^{3+}$ and Iron $Fe^{3+}$ have been noted, and there is some speculation that in at least some situations, ionic gallium may compete with the ionic form of iron in various biochemical reactions. However because the reaction properties of gallium may otherwise not resemble those of iron, this may cause distortion or inhibition of those biochemical reactions that require iron.

Although the mechanism of action has not yet been fully elucidated, gallium nitrate also appears to inhibit the calcium turnover (resorption) in bone, thus reducing the amount of circulating calcium in the blood.

Gallium nitrate is presently FDA approved as a prescription intravenous infusion for the treatment of cancer related hypercalcemia (excessively high levels of calcium), and is presently sold for this purpose by Genta Inc, under the trade name Ganite®.

The ability of gallium nitrate in solid form to favorably enhance the later stages of the wound healing process (i.e. the later stages of inflammation and proliferation) was disclosed in a series of patents by Bockman et. al., including U.S. Pat. Nos. 5,556,645, 5,686,116, and 6,165,514, and 6,287,606. There is also some suggestion in the literature (Panagakos, et. al., "The effect of gallium nitrate on synoviocyte MMP activity", Biochimie. 2000 February; 82(2):147-51) that gallium nitrate can inhibit matrix metalloproteinase (MMP) activity. More recently, Chich-Chang Chu et. al., in US patent application 2007/0155273, proposed a non-woven fabric bandage incorporating solid gallium nitrate in order to promote the later stages of wound healing, which as previously discussed begin after hemostasis has been established, and typically operate over a period of days or weeks.

There appears to be no suggestion in the prior art that various forms of Gallium nitrate are in any way useful for promotion of the very earliest stages of hemostasis—either coagulation, platelet activation, or clot formation. As will be discussed, this may be because the liquid formulation of gallium nitrate commonly used for medical purposes may at least partially mask the hemostasis promoting aspects of gallium nitrate.

BRIEF SUMMARY OF THE INVENTION

Surprisingly, it was found that liquid gallium nitrate solutions, applied directly to bleeding open wounds (rather than indirectly by intravenous infusion, which is its typical medical use) are very effective at the immediate treatment of these wounds, and the promotion of the early stages of hemostasis.

This unexpected finding was the result of an accidental event in which an aqueous solution of 14% gallium nitrate, originally intended for a non-medical application, was instead unintentionally applied to the surface of a large open wound immediately after wound formation. Although a wound of that size would normally be expected to bleed for at least many minutes, the accidental exposure to the non-medical gallium nitrate solution instead resulted in unexpectedly rapid clot formation, as well as near immediate reduction in pain.

This unexpected finding, in conjunction with various follow-on experiments, has demonstrated the utility of incorporating gallium nitrate into pharmaceutical compositions for use in the treatment of open wounds, as well as a new method for treating open wounds.

These new pharmaceutical compositions for treatment of open wounds are generally based upon application of liquid (aqueous) gallium nitrate to the open wounds. As will be discussed, the aqueous gallium nitrate may be administered by many different types of pharmaceutical vehicles, including sprays, ointments, foams, creams, topical lotions, liquid activated bandages, liquid bandages and even enemas (e.g. for applications such as ulcerative colitis). The aqueous gallium nitrate may be either used as a stand-alone ingredient, or alternatively as part of a more complex pharmaceutical composition containing one or more other active and inactive ingredients.

DETAILED DESCRIPTION OF THE INVENTION

Figure 1:
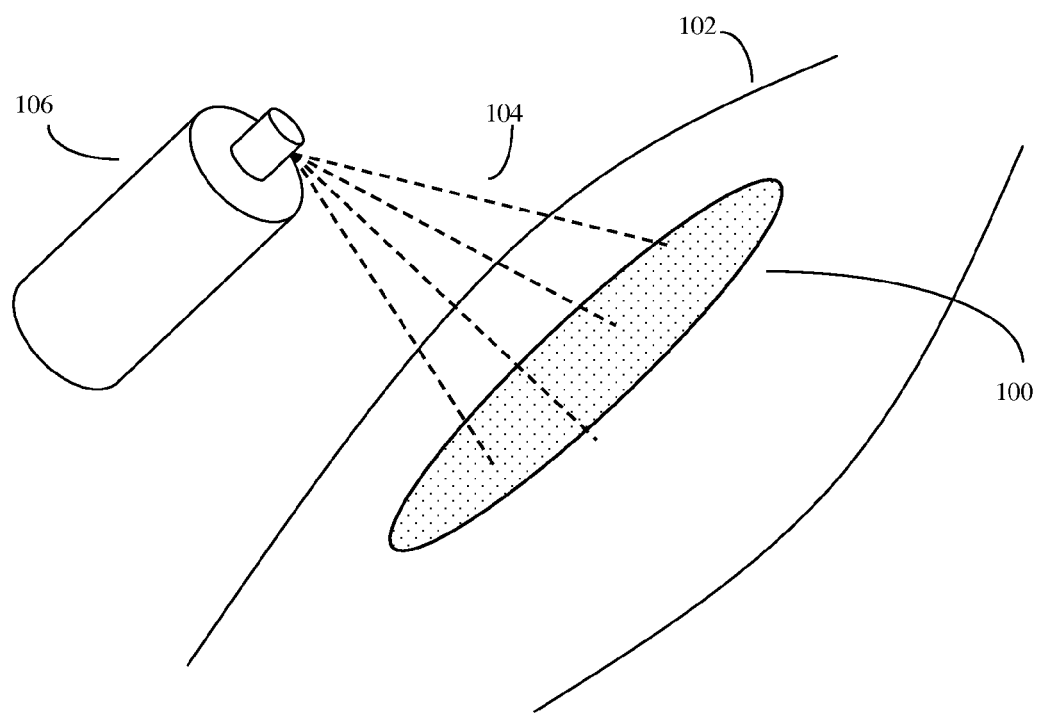
FIG. 1 shows a gallium nitrate spray being applied to an open wound

The utility of topical gallium nitrate for the earliest stages of wound treatment has not been previously reported. Indeed, the official Food and Drug Administration (FDA) indication for aqueous gallium nitrate solutions is instead for intravenous administration and injection. These approved medical applications would generally require that aqueous gallium nitrate not induce blood clotting or other early stages of hemostasis, such as platelet aggregation, generally required in the initial stages of wound treatment.

How might this apparent paradox between the unexpected observations regarding the clinical utility of topical aqueous gallium nitrate in the earliest stages of wound treatment (which prompted this disclosure), and the previous medical use of infused gallium nitrate in situations where blood clotting and/or platelet aggregation were undesirable, be reconciled?

One possible explanation may be that previous clinical work with gallium nitrate strongly tended to teach compounding the aqueous gallium nitrate solutions with large amounts of sodium citrate. The sodium citrate was ostensibly used to help buffer the gallium nitrate solutions to a more neutral pH (needed for injection), as well as improve the stability of the resulting gallium nitrate solution.

Thus the FDA approved form of the material, Ganite® (Genta Inc., Berkeley Heights, N.J.), uses the citrate form. Further, Bernstein, (Chapter 14 of *Metallotherapeutic Drugs and Metal-Based Diagnostic Agents: The use of Metals in Medicine*, Gielen and Tekink editors, (2005), John Wiley & Sons, Ltd.) teaches on page 261 that the citrate form of this material is the usual form used for medical applications.

Thus, Genta in the website, http://www.drugs.com/pro/ganite.html, teaches creation of dilute solutions of gallium nitrate for intravenous administration by first reacting gallium in the elemental form with nitric acid, purifying the resultant $Ga(NO_3)_3$ salt by recrystalization, and creating a $Ga(NO_3)_3 \cdot 9H_2O$ crystalline powder. This powder is then dissolved in water with sodium citrate, to a concentration of about 25 mg/ml gallium nitrate and 28.75 mg/ml sodium citrate dehydrate, and adjusted to approximately neutral physiological pH (i.e. between 6.0 to 7.0) by titration with sodium hydroxide and hydrochloric acid.

As another example, Warrell et. al. (J, Clin. Invest. 73 (1984) 1487-1490) teaches production of dilute aqueous solutions of gallium nitrate by dissolving the anhydrous form of the $Ga(NO_3)_3$ crystalline powder in water at a concentration of 10 mg/ml anhydrous gallium nitrate, along with 11.5 mg/ml trisodium citrate. Warrell further teaches including 0.9% NaCl into this solution to keep the solution roughly isotonic, and again adjusting the pH to around 7.0 with sodium hydroxide.

One drawback of confining medical investigations of aqueous gallium nitrate to only gallium nitrate—citrate solutions is that added citrate greatly interferes with the blood coagulation processes that commence at the earliest stages of wound formation and hemostasis. Indeed citrate in various forms (i.e. acid citrate dextrose, sodium citrate) is commonly used to prevent blood coagulation in both blood taken for transfusion purposes (i.e. blood banking), as well as keeping blood samples in a non-coagulated form for laboratory analysis of the earliest stages of the clotting system, such as prothrombin time assays.

However, particularly for topical administration to fresh wounds, where induction of the earliest stages of hemostasis (i.e. coagulation, platelet aggregation, etc.) is in fact desirable, investigation of alternative formulations of gallium nitrate, that do not also include anticoagulants (such as citrate) in the formulation, may be desirable.

Thus although the aqueous citrate form of gallium nitrate may be used for this invention, in an alternative embodiment, which may be particularly useful for maintaining hemostasis, aqueous gallium nitrate solutions intended for topical use can be prepared without the addition of citrate or other materials that can act to block the action of the blood coagulation pathway.

In one embodiment, an aqueous form of gallium nitrate, which may not be suitable for direct intravenous injection, but which may be quite compatible for topical use, may be prepared by directly dissolving the $Ga(NO_3)_3$ salts in water at concentrations higher than the 1% concentration typically used for intravenous injection purposes. In a preferred embodiment, still higher concentrations, often between about 2% and 20% weight/volume of gallium nitrate/water, occasionally as high as 42%, and preferably in the 5% to 15% range weight/volume range may be adequate as a basis for a variety of different topical treatments for fresh wounds.

Initial Experiments Demonstrating the Utility of Topical Gallium Nitrate for Fresh Wounds Unless otherwise specified, all experiments below used an aqueous solution of unbuffered $Ga(NO_3)_3$, dissolved in water in the 5% to 15% weight/volume concentration range, specifically as stated. Note that none of these formulations contained citrate.

EXPERIMENT 1

A first human subject sustained an accidental 1-inch long gash to the index finger, deep enough to extend below the epidermis, but stopping short of the bone. The wound bled profusely and hurt intensely. Subject immediately inserted the finger into a solution of concentrated (non-medical) 14% aqueous gallium nitrate. Immediately after application of gallium nitrate, the flowing blood began changing to a brownish color, and the bleeding subsequently stopped within a few seconds—unusually rapidly for a wound of this size and depth. Subject kept the finger in the 14% aqueous gallium nitrate solution for 10 minutes. Upon removal from the solution, the wound was no longer bleeding, and no pain was felt. A regular bandage was then applied. Although a wound of this depth would normally require stitches, by the time further medical treatment was sought, stitches were no longer deemed necessary. The wound healed completely within a matter of days, with no recurring pain or subsequent bleeding.

EXPERIMENT 2

A different (second) human subject sustained an accidental 1-inch wide gash to the chin which again penetrated the epidermis, stopped short of the bone, and which bled very profusely. The wound was treated by liberally applying the same type of 14% gallium nitrate solution used in Experiment 1. As before, the color of the blood immediately changed to a brownish color and the wound rapidly stopped bleeding. The resulting clot was so tight that a treating physician, examining the wound shortly thereafter, remarked on its unusual strength.

One potential side effect of the rapid gallium nitrate facilitated wound closure was noted. This was that although the gallium nitrate solution appeared to cause the wound to seal with unusual strength and speed, if the wound is not fully cleaned in advance, this can be a drawback, because the wound must therefore be reopened for subsequent cleaning. This suggests that in "dirty wound" situations, preliminary irrigation of the wound with a cleansing solution, such as an isotonic saline solution, prior to administration of a gallium nitrate based topical treatment may be desirable.

EXPERIMENT 3

A third human subject sustained an accidental 2-inch wide and quite deep gash (penetrating the epidermis, stopping short of the bone) to the top of the forehead, accompanied by profuse bleeding. A less concentrated (7% aqueous gallium nitrate) topical solution was then applied. As before, the color of the blood immediately changed, and the wound stopped bleeding unusually quickly.

EXPERIMENT 4

The bleeding time test measures the function of a number of coagulation pathway parameters, including platelet function, extrinsic coagulation pathway and intrinsic coagulation pathway. Here, in order to better understand the various coagulation pathways that might be impacted by gallium nitrate, a bleeding function experiment was done to see if the gallium nitrate effect worked for patients (e.g. Warfarin or Coumadin™ patients) with a suppressed extrinsic coagulation pathway.

Does gallium nitrate act to reduce bleeding time for patients on oral anticoagulants?

In this experiment, a first subject (Subject 1) was treated with Coumadin™ (Warfarin) to achieve a therapeutic dose with an International Normalized Ratio (INR) of 2.5.

Subject 1: To induce bleeding, the first INR 2.5 subject's mid forearm was punctured with a #11 scalpel blade to a depth of 4 mm. This produced prompt flow of blood in the form of a steady slow blood stream down the subject's forearm. This blood flow was gently wiped with gauze every 30 seconds without applying pressure. Under these control (no gallium nitrate) conditions, the bleeding stopped at 122 seconds.

To investigate the effect of gallium nitrate, a second puncture was then made to the arm of the INR 2.5 subject following the same methods as for the first puncture. However in this portion of the experiment, at 5 seconds after puncture, once blood flow had commenced, a gallium nitrate (14%) solution was applied using a soaked cotton-ball. In contrast to the previous no-gallium control, in this gallium nitrate application experiment, blood flow ceased after only 35 seconds. A small pool of blood stayed about incision site. Thus for an INR 2.5 patient, gallium nitrate reduced bleeding time from a control of 122 seconds to a value of only 35 seconds, which is a very substantial decrease.

To see if there were any substantial differences with a non-Warfarin/Coumadin treated subject, at the same time and under the same conditions, a non-Coumadin treated subject, (subject 2) was examined.

Subject 2: A mid forearm puncture was made following the same methods as described above. This first puncture was gently wiped with gauze every 30 seconds without applying pressure. In this no gallium nitrate control condition, bleeding stopped at 268 seconds To investigate the effect of gallium nitrate, a second puncture was then made following the same methods as for the first puncture. At 5 seconds after puncture, once blood flow had commenced, a gallium nitrate (14%) solution was applied using a soaked cotton-ball. By 77 seconds the flow had ceased and a visible clot had started to form.

In this experiment, gallium nitrate reduced bleeding time from an open wound by approximately 75% when compared to control no-gallium nitrate conditions in both a Warfarin/Coumadin treated subject and a non-Warfarin/Coumadin treated subject.

Interestingly, whilst gallium nitrate stemmed the flow of blood in both subjects, the Coumadin treated subject did not form a visible clot whilst the non-Coumadin treated subject formed a very visible brown clot.

Without wishing to be bound by any particular theory, the observation that the gallium nitrate effect works well in individuals with inhibited extrinsic coagulation pathway lends some support for the theory that the gallium nitrate may be mediating its effects through other coagulation pathways, possibly including platelets or the intrinsic coagulation pathway. However the observed differences in clot structure suggest that the extrinsic coagulation pathway may at least play a secondary role in the gallium nitrate effect.

Experiment 4 also shows that gallium nitrate may be useful for patients suffering from various types of clotting disorders.

Future planned work includes additional controlled experiments that will further investigate the difference in speed of hemostasis formation between the gallium nitrate treatment arm, and various non-treatment and normal-wound-treatment arms.

These initial experiments suggest that in many situations, it may be useful to package the gallium nitrate formulation as part of a wound treatment kit. This wound treatment kit may contain multiple components. Examples of such multiple components include a 1) preliminary wound wash, such as a saline solution intended to remove dirt and debris from the fresh wound prior to treatment by the gallium nitrate formulation. 2) a topical gallium nitrate formulation, which can be of various types (described below). 3) a bandage to cover the wound after use of the topical gallium nitrate formulation.

Variant Formulations:
Use of Alternative Gallium Salts

Although gallium nitrate has been used throughout this disclosure as an example of one specific gallium salt that may used in certain specific embodiments of the invention, in alternative embodiments, other gallium salts may also be used. Examples of such alternatives include gallium phosphate, gallium citrate, gallium chloride, gallium fluoride, gallium carbonate, gallium formate, gallium acetate, gallium tartrate, gallium maltol, gallium oxalate, and gallium oxide. Other forms may include gallium pyrones, gallium pyridines, gallium hydroxymates, gallium aminocarboxylates, gallium 8-quinolinolate, (tris(8-quinolinolato) gallium(III), gallium maltolate (tris-3-hydroxy-2-methyl-4H-pyran-4-onato)gallium(III), and other physiologically compatible aqueous gallium salt solutions.

Formulation Variants:

In general, the formulation variants of the aqueous gallium nitrate and other gallium salts intended for topical administration for wound treatment may follow examples from Allen et. al., "*Ansel's pharmaceutical dosage forms and drug delivery systems, eighth edition*" Lippincott Williams & Wilkins, (2004). Other formulation variants that may be used include variants taught by Bernstein for oral gallium compositions in U.S. patent application Ser. No. 11/551,815 (2007/0098815), incorporated herein by reference.

Although the aqueous gallium nitrate solution may be applied directly to the wound as a lotion, foam, or spray, in many situations, it will be advantageous to include other inactive or active ingredients into the formulation.

Examples of inactive formulation ingredients include thickening or viscosity enhancing agents, which may enhance the ability of the applied gallium nitrate solution to adhere to the wound.

Such thickening agents that can be included in the topical gallium nitrate formulations can include various cellulose derivatives, including carboxymethylcellulose, hydroxypropylmethylcellulose, and methylcellulose. Other pharmaceutically acceptable thickening agents, such as carbopols, polyethylene glycol, gum Arabic, xanthum gum may also be used. In general, any pharmaceutically acceptable thickening agent that is either relatively stable in the presence of the aqueous gallium salt of interest, or that can be co-stored with the aqueous gallium salt of interest (e.g. in a different phase of an emulsion) is within the scope of this invention.

Gallium nitrate and other gallium salts have a naturally occurring antibacterial activity, possibly related to the inhibitory effect of gallium on iron requiring biochemical reactions, which is an additional benefit for using these chemicals for wound treatment. However in certain formulations, using additional active ingredients with antibacterial activity may also be useful.

Examples of active ingredients that may be included in the topical gallium nitrate formulation, either directly or as part of the opposite phase of an emulsion, include antiseptics, antibiotics and the like. Examples of suitable antibiotics include bacitracin, polymyxin b, neomycin, polysporin, Neosporin, povidone-iodine and the like.

Other antibacterial agents may also be incorporated into the topical gallium nitrate formulation, including silver sulfadiazine, mafenide acetate, nystatin, nitrofurazone, gentamicin, and the like.

Other potentially useful agents that may also be included in the formulation include acetic acid, silver nitrate, and chlorhexidine gluconate.

Other compositions may include other pharmaceutically compatible absorption enhancers, buffers, carriers, coating agents, colorants, controlled release agents, diluents, emulsifiers, preservatives, propellants, stabilizers vehicles, and the like.

Other wound healing agents may be used as well, including *aloe vera* gel, corticosteroids, naltrexone, fibrin, enzymes, silver nitrate, growth factors, ecabet sodium, zinc oxide, and antibodies, and the like.

Emulsion Based Formulations

Gallium salts will normally dissolve readily in water. In some embodiments however, other optional active or inactive formulation ingredients may either not dissolve readily in water, or alternatively should be kept somewhat separate from the aqueous gallium salt component for better storage stability. In still other situations, use of foams, creams, or other more complex topical administration modalities may be preferred. In these situations, emulsion based formulations, using two or more immiscible liquids, may be desirable. Here usually one immiscible liquid will be water, and the second may be a more hydrophobic liquid such as oil (for example soybean oil), an alcohol, or the like.

In general, such emulsions may be formulated according to the methods described by "*Pharmaceutical Emulsions and Suspensions, $2^{nd}$ edition*", Nielloud and Marti-Mestres editors, Informa Healthcare, (2000).

Depending upon the relative proportions of the aqueous and non-aqueous portions of the emulsion, the resulting emulsion may be applied as a spray, topical solution, cream, foam, ointment, or liniment.

The storage stability of the emulsion may be further facilitated by use of pharmaceutically acceptable emulsifiers, surfactants, or detergents, including cetearyl alcohol, ceteareth 20, emulsifying wax, lecithin, polysorbate 20, and the like.

Methods of Topical Treatment:

The liquid gallium nitrate (or other gallium salt) solutions may be applied to wounds in a variety of different topical solution and topical tincture dosage forms, including, but not limited to, sprays, foams, topical solutions, suspensions, lotions, ointments, creams, gels, enemas, liquid bandages, bandages with a liquid component. Here, some of these alternative dosage forms will be discussed in some detail.

Sprays

In one embodiment, the liquid gallium nitrate may be presented in a spray bottle (either manually pumped, or in a pressurized container), and the solution sprayed directly onto an open wound, followed by further treatment (i.e. compression, bandages, etc.) as appropriate.

As previously discussed, if used in a spray form, in some embodiments, it may be desirable to modify the properties of the aqueous gallium nitrate solution by adding viscosity enhancing agents, antibiotics, and other wound healing agents as appropriate.

An example of a spray based topical gallium nitrate formulation is shown in FIG. 1. Here an open wound (100) on a skin surface (102) is being treated by a spray of a liquid gallium nitrate formulation (104) from a pressurized or pump operated container (106).

Foams:

In some situations, it may be desirable to incorporate additional agents into the gallium nitrate solution to induce foaming. Indeed, it may be desired that a relatively stiff foam adhere to the wound surface for a period of time, protecting the wound from the drying effects of the air. Such foaming agents may include oil-water mixtures and emulsions, as well as additional agents needed to stabilize the foam.

Emulsion Based Formulations (Creams, Ointments, etc.)

Creams: Creams are oil in water emulsions in which the amount of water is greater than the amount of oil.

Figure 2:
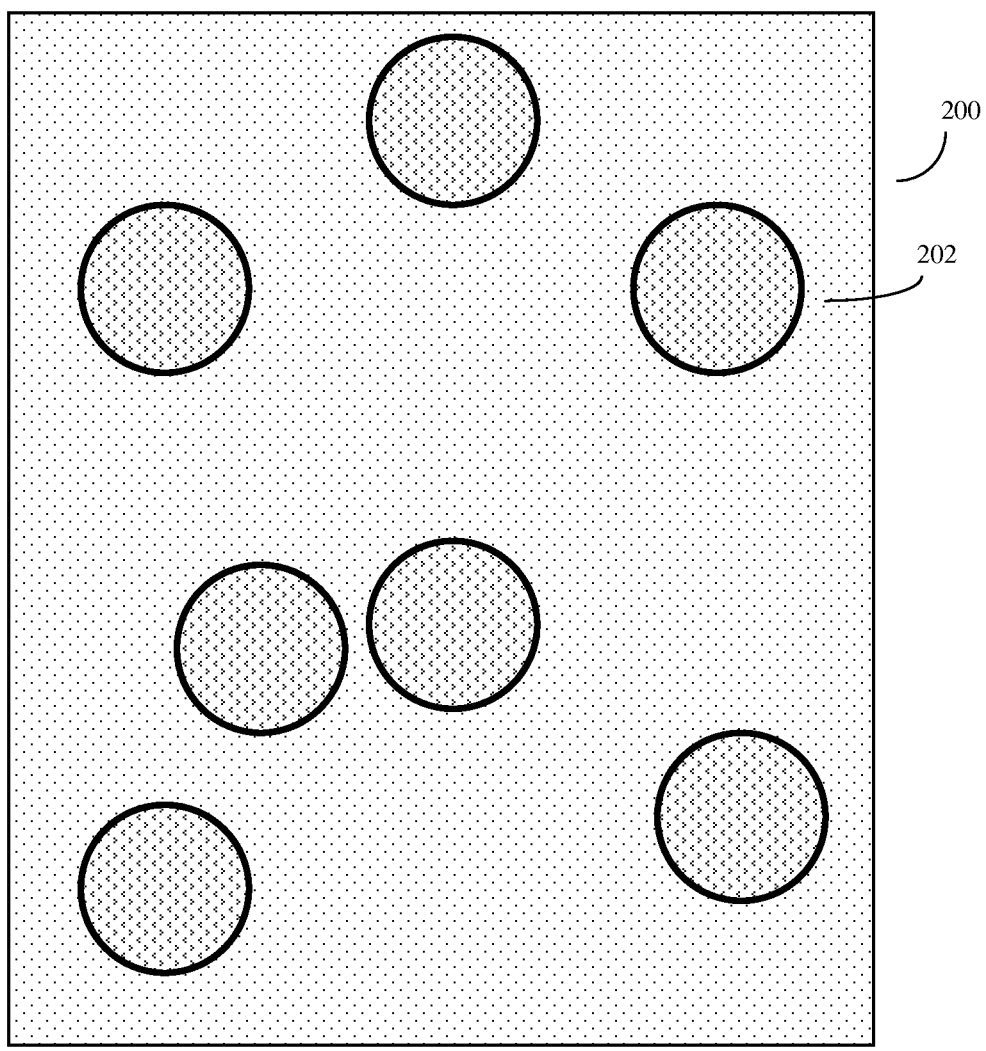
FIG. 2 shows a gallium nitrate emulsion. Here the majority of the emulsion is an aqueous phase and contains the dissolved gallium nitrate. The hydrophobic liquid phase component of the emulsion is in the form of microscopic droplets, and may contain one or more of the other active or inactive formulation ingredients.

An example of what a cream based emulsion looks like at the microscopic level is shown in FIG. 2. In FIG. 2 (200), the aqueous phase of the solution, normally containing the dissolved gallium nitrate or other gallium salt, is the main component of the formulation (200). The second fluid, which is immiscible with the main aqueous component, and which frequently will be an alcohol or oil, forms microscopic droplets suspended within this aqueous phase (202). This second phase may contain other active or inactive formulation ingredients, and is a particularly good vehicle for including some of the more hydrophobic formulation ingredients or ingredients that may not be entirely compatible for storage in the gallium nitrate aqueous phase. The microscopic droplets are normally kept in a stable suspension by use of emulsifier agents, discussed elsewhere.

By contrast, in ointments, the relative proportions of the aqueous phase and the non-aqueous phase (usually oil phase) are reversed, and the non-aqueous phase dominates. Because ointments will usually contain more oil, which will tend to not evaporate, such gallium nitrate based ointments may be suitable for situations where it is desired to cover the wound with the topical agent for a considerable period of time.

Liquid Bandage Variants

In other embodiments of the invention, it may be useful to include polymers, such as polyvinylpyrrolidone, medical cyanoacrylates (e.g. octylcyanoacrylates) acrylate copolymers, pyroxylin/nitrocellulose, acrylate or siloxane into the gallium salt formulation, either directly, or as part of the non-aqueous component of an emulsion, so that upon drying, the polymeric component forms a layer that binds to the skin.

Dry-Liquid Bandage Variants

In other embodiments of the invention, it may be useful to construct bandages that contain either ampoules or small capsules of liquid gallium nitrate solution within the matrix of the bandage. In this embodiment, the user would first activate the bandage by breaking the ampoules or capsules of liquid gallium nitrate, thus saturating the bandage with the liquid gallium nitrate solution, before applying the bandage to the wound. This embodiment is shown in FIG. 3.

Figure 3:
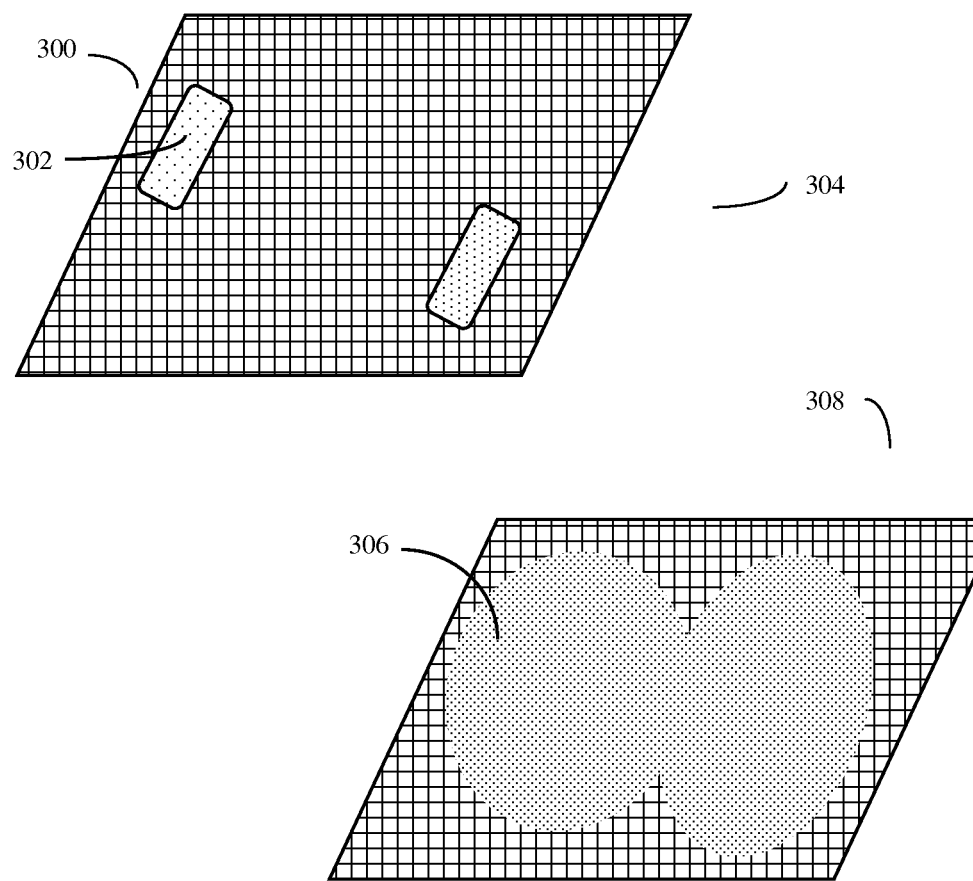
FIG. 3 shows a bandage containing or packaged with one or more breakable ampoules or capsules of aqueous gallium nitrate.

As shown in FIG. 3 a bandage consisting of a woven or nonwoven fabric, preferably sterile (300) contains one or more small vials, capsules, or ampoules of liquid gallium nitrate solution (302). In the non activated state, the bandage is dry (304). However in the activated state, the user breaks the vials, capsules or ampoules of liquid gallium nitrate, saturating the bandage with the liquid solution (306) prior to applying the now wet bandage (308) to the fresh wound.

Applications to Hemophilia and Other Clotting Disorders

In addition to facilitating hemostasis in subjects with normal coagulation capability, topical application of aqueous gallium salts, in particular gallium nitrate may also be useful for establishing hemostasis in subjects with abnormal coagulation function, such as hemophilia. Without being bound to a particular theory, this may be because the gallium nitrate may act to bypass the coagulation factor defect (e.g. the clotting factor VIII deficiency in Hemophilia A, and/or the factor IX deficiency found in Hemophilia B).

Applications to Internal Wounds

In addition to the external wound applications previously discussed, aqueous gallium salts may also be useful for treating various internal wounds as well. These wounds can be surgical wounds, such as are often produced during surgery, and here the various gallium salts may be applied to various surgical wounds according to the various previously discussed formulations. Additionally, there are other disorders that cause internal wounds, such as various inflammatory bowel diseases, (e.g. ulcerative colitis) where various forms of gallium salts, either in the form of a suppository, or in the form of an enema may also be useful.

The invention claimed is:

1. A method to rapidly control bleeding and reestablish hemostasis in fresh open wounds, the method comprising the steps of:
    (a) providing a topical formulation of an aqueous gallium salt at a concentration of about 1-42% salt weight/water weight of said gallium salt, wherein said gallium salt is selected from the group consisting of: gallium nitrate, gallium phosphate, gallium citrate, gallium chloride, gallium carbonate, gallium formate, gallium tartrate, gallium oxalate, and gallium oxide;
    (b) encasing said topical formulation into one or more capsules;
    (c) providing said capsules in a woven or non-woven bandage, wherein said capsules are adapted to release said topical formulation into said bandage upon said capsules being ruptured; and
    (d) applying said bandage to a fresh open wound to control bleeding and reestablish hemostasis in about 10 minutes or less.

2. The method of claim 1, wherein said gallium salt is gallium nitrate.

3. The method of claim 1, wherein said topical formulation is an aqueous formulation of a gallium salt.

4. The method of claim 1, wherein said topical formulation further comprises additional components selected from the group consisting of: cellulose derivatives, carbopols, polyethylene glycol, gum Arabic, or xanthum gum.

5. The method of claim 1, wherein said topical formulation further comprises additional components selected from the group consisting of: bacitracin, polymyxin b, neomycin, polysporin, Neosporin, povidone-iodine, silver sulfadiazine, mafenide acetate, nystatin, nitrofurazone, gentamicin, acetic acid, silver nitrate, and chlorhexidine gluconate.

6. The method of claim 1, wherein said topical formulation further comprises pharmaceutically-compatible agents selected from the group consisting of: absorption enhancers, buffers, carriers, coating agents, colorants, controlled release agents, diluents, emulsifiers, preservatives, propellants, and stabilizer vehicles.

7. The method of claim 1, wherein said topical formulation further comprises wound-healing agents selected from the group consisting of: aloe vera gel, corticosteroids, naltrexone, fibrin, enzymes, silver nitrate, growth factors, ecabet sodium, zinc oxide, and antibodies.

8. The method of claim 1 wherein said topical formulation further comprises polymers that are adapted to form a layer upon drying that binds to skin; said polymers selected from the group consisting of: polyvinylpyrrolidone, medical cyanoacrylates, pyroxylin/nitrocellulose, acrylate, and siloxane.

9. A kit to control bleeding and reestablish hemostasis in fresh open wounds, the kit comprising:
    (a) an aqueous solution of a gallium salt at a concentration of about 1-42% salt weight/water weight of said gallium salt, wherein said gallium salt is selected from the group consisting of: gallium nitrate, gallium phosphate, gallium citrate, gallium chloride, gallium carbonate, gallium formate, gallium tartrate, gallium oxalate, and gallium oxide;

(b) a bandage; and (c) instructions for use of said gallium salt solution and said bandage to control bleeding and reestablish hemostasis in a fresh open wound in about 10 minutes or less.

10. A pharmaceutical composition to control bleeding and reestablish hemostasis in fresh open wounds, the composition comprising:

(a) a topical formulation of an aqueous gallium salt at a concentration of about 1-42% salt weight/water weight of said gallium salt, wherein said gallium salt is selected from the group consisting of: gallium nitrate, gallium phosphate, gallium citrate, gallium chloride, gallium carbonate, gallium formate, gallium tartrate, gallium oxalate, and gallium oxide, said topical formulation controls bleeding and reestablishes hemostasis in a fresh open wound in about 10 minutes or less.

11. The pharmaceutical composition of claim 10, wherein said topical formulation is administered as a rinse, lotion, or spray.

12. The pharmaceutical composition of claim 10, wherein said topical formulation is an emulsion of a gallium salt in an aqueous phase and a non-miscible liquid suspended in small droplets in a non-aqueous phase.

13. The pharmaceutical composition of claim 12, wherein said topical formulation is administered as a rinse, lotion, spray, foam, cream, suppository, or ointment.

14. The pharmaceutical composition of claim 10, wherein said topical formulation is encased into one or more capsules provided in a woven or non-woven bandage; and wherein said capsules are adapted to release said topical formulation into said bandage upon said capsules being ruptured.

15. The method of claim 1, wherein said step of applying is adapted to control bleeding and reestablish hemostasis in about 77 seconds or less.

16. A method to rapidly control bleeding and reestablish hemostasis in fresh open wounds, the method comprising the steps of:

(a) providing a topical formulation of an aqueous gallium salt at a concentration of about 1-42% salt weight/water weight of said gallium salt, wherein said gallium salt is selected from the group consisting of: gallium nitrate, gallium phosphate, gallium citrate, gallium chloride, gallium carbonate, gallium formate, gallium tartrate, gallium oxalate, and gallium oxide; and (b) applying said topical formulation to a fresh open wound to control bleeding and reestablish hemostasis in about 10 minutes or less.

* * * * *